United States Patent [19]

Eidenschink et al.

[11] 4,382,012
[45] May 3, 1983

[54] LIQUID CRYSTALLINE DIKETONES

[75] Inventors: Rudolf Eidenschink, Dieburg; Ludwig Pohl, Darmstadt, both of Fed. Rep. of Germany

[73] Assignee: Merck Patent Gesellschaft mit beschraenkter Haftung, Darmstadt, Fed. Rep. of Germany

[21] Appl. No.: 283,844

[22] Filed: Jul. 16, 1981

Related U.S. Application Data

[62] Division of Ser. No. 148,353, May 9, 1980, Pat. No. 4,297,515.

[30] Foreign Application Priority Data

May 10, 1979 [DE] Fed. Rep. of Germany ....... 2918775

[51] Int. Cl.³ .......................... G02F 1/13; C09K 3/34
[52] U.S. Cl. .............................. 252/299.1; 252/299.5; 252/299.63; 252/299.66; 350/350 R
[58] Field of Search ........................ 350/350 R, 349; 252/299.5, 244.63, 299.66, 299.1

[56] References Cited

U.S. PATENT DOCUMENTS

| | | | |
|---|---|---|---|
| 3,947,375 | 3/1976 | Grat et al. | 252/299.66 |
| 3,983,049 | 9/1976 | Aftergut et al. | 252/299.5 |
| 4,011,173 | 3/1977 | Steinstrasser | 252/299.5 |
| 4,130,502 | 12/1978 | Eidenschink et al. | 252/299.63 |
| 4,154,697 | 5/1979 | Eidenschink et al. | 252/299.63 |
| 4,229,315 | 10/1980 | Krause et al. | 252/299.63 |
| 4,293,193 | 10/1981 | Labes et al. | 252/299.5 |
| 4,297,515 | 10/1981 | Eidenschink et al. | 568/329 |
| 4,330,426 | 5/1982 | Eidenschink et al. | 252/299.63 |

FOREIGN PATENT DOCUMENTS

| | | | |
|---|---|---|---|
| 2031010 | 4/1980 | United Kingdom | 252/299.65 |
| 779380 | 11/1980 | U.S.S.R. | 252/299.66 |

Primary Examiner—Teddy S. Gron
Attorney, Agent, or Firm—Millen & White

[57] ABSTRACT

Diketones of the formula

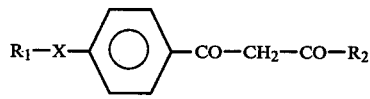

wherein $R_1$ is alkyl, perfluoroalkyl or alkoxy, each of 1–18 carbon atoms; $R_2$ is alkyl or perfluoroalkyl, each of 1–12 carbon atoms; and X is 1,4-trans-cyclohexylene, 1,4-phenylene or 4,4'-cyclohexylphenyl are liquid crystalline compounds.

7 Claims, No Drawings

LIQUID CRYSTALLINE DIKETONES

This is a division, or application Ser. No. 148,353, filed May 9, 1980, now U.S. Pat. No. 4,297,515.

BACKGROUND OF THE INVENTION

For liquid crystal display elements, the properties of nematic or nematic-cholesteric liquid crystalline materials are utilized to effect a significant change in their optical properties, such as light transmission, light scattering, double refraction, reflectance or color, under the influence of electrical fields. The function of such display elements is based, for example, on the phenomenon of dynamic scattering, the deformation of aligned phases, the Schadt-Helfrich effect in the twisted cell or the nematic-cholesteric phase transition.

For industrial application of these effects in liquid crystal display elements, liquid crystalline materials are needed which have to meet a large number of requirements. Particularly important requirements are chemical stability towards moisture, air and physical influences, such as heat, radiation in the infrared, visible and ultraviolet ranges and steady and alternating electrical fields. Furthermore, a liquid crystal mesophase in the temperature range from at least 0° C. to +50° C., and preferably from −10° C. to +70° C., and a viscosity at room temperature of not more than 60 cP are demanded for liquid crystalline materials which can be used industrially. Finally, these materials must not have any characteristic absorption in the range of visible light, that is to say they must be colorless.

A number of liquid crystalline compounds are already known which meet the stability requirements demanded of dielectrics for electronic components and which are also colorless. These include, in particular, the p,p'-disubstituted phenyl benzoates described in German Offenlegungsschrift No. 2,139,628, the p,p-disubstituted biphenyl derivatives described in German Offenlegungsschrift No. 2,356,085 or the phenylcyclohexane derivatives described in German Offenlegungsschrift No. 2,636,684.

These categories of liquid crystalline substances, and also other categories of liquid crystalline substances used hitherto in practice, are built up from aromatic or hydroaromatic rings which have terminal alkyl and/or alkoxy groups and are linked to one another directly or via a bridge group. This structure ensures the rigidity of the molecule necessary for a liquid crystalline mesophase, and in particular a nematic mesophase, to occur. However, many of these compounds have relatively little polar character and are therefore frequently not suitable for dissolving polar doping agents and/or dichroitic dyes in the concentrations which are desired for some types of applications.

SUMMARY OF THE INVENTION

Accordingly, it is an object of this invention to provide liquid crystalline compounds of polar character in which even strongly polar doping agents and/or dichroitic dyes are soluble to a sufficient extent to enable color switches based on the guest-host effect to be produced.

Upon further study of the specification and appended claims, further objects and advantages of this invention will become apparent to those skilled in the art.

These objects have been attained, surprisingly, by the discovery that the diketones of Formula I

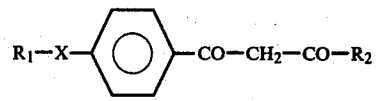

wherein $R_1$ is alkyl, perfluoroalkyl or alkoxy, each of 1–18 carbon atoms; $R_2$ is alkyl or perfluoroalkyl, each of 1–12 carbon atoms; and X is 1,4-trans-cyclohexylene, 1,4-phenylene or 4,4'-cyclohexylphenyl, are outstandingly suitable as components of polar liquid crystal dielectrics.

The compounds of Formula I possess liquid crystal mesophases and, because of their polar character, are able to dissolve strongly polar doping agents and/or dichroitic dyes in concentrations hardly achieved hitherto. Furthermore, the compounds of Formula I are able to form salts and complex compounds with metal ions. These salts and complexes can be used as doping agents effecting the necessary electrical conductivity in liquid crystal dielectrics for dynamic scattering. Finally, they possess an outstanding stabilizing effect on those liquid crystalline compounds which are sensitive to visible light and UV radiation.

The invention thus relates to the diketones of Formula I, a process for their preparation, and their use as components of liquid crystal dielectrics.

The invention also relates to liquid crystal dielectrics which contain at least one compound of Formula I and to electro-optical display elements which are based on a liquid crystal cell and contain a dielectric of this type.

As can be seen, the diketones of this invention are 4-cyclohexylacetophenone derivatives of Formula Ia

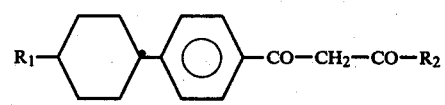

or 4-phenylacetophenone derivatives of Formula Ib

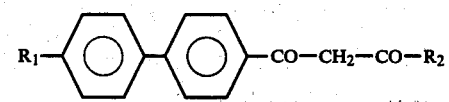

or 4-(4-cyclohexylphenyl)-acetophenone derivatives of Formula Ic

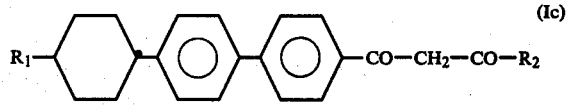

in which partial Formulae Ia to Ic, the radicals $R_1$ and $R_2$ are as defined for Formula I. The trans-configuration of the cyclohexane rings in Formulae Ia and Ic is shown by the black dot on the right-hand side of the respective ring.

DETAILED DISCUSSION

In the compounds of this invention, $R_1$ is alkyl, alkoxy or perfluoroalkyl each of 1–18 carbon atoms, which can be straight-chain or branched. Among the straight-chain radicals $R_1$, i.e., methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl or n-octadecyl and the analogous alkoxy or perfluoroalkyl groups, those with not more than 12 carbon atoms are preferred.

Occasionally, however, compounds of Formula I which contain branched substituents $R_1$ are also of importance, since these compounds sometimes display better solubility characteristics in the customary liquid crystal base mixtures. Substituents $R_1$ of this type which are not straight-chain preferably contain not more than one branch in the chain. Preferred branched substituents are those in which the carbon chain is branched at the carbon atom adjacent to the group X or, in particular, at one of the two nearest carbon atoms. Important groups among these substituents include those branched groups in which a methyl or ethyl group is located in the 1-, 2- or 3-position on a relatively long carbon chain, for example, isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl or 1-methylheptyl. These selection criteria also apply analogously for the corresponding alkoxy groups $R_1$.

If $R_1$ is a perfluoroalkyl group, preferred groups are those which contain not more than 8 carbon atoms and, in particular, those with 1-5 carbon atoms; among such compounds, those in which $R_1$ is trifluoromethyl are particularly easily accessible. For the compounds of the partial Formulae Ia and Ic, preferred compounds are those in which $R_1$ is an alkyl group; because the synthesis of the corresponding alkoxy and perfluoroalkyl derivatives is more difficult, the use of these derivatives in liquid crystal dielectrics is less economical.

In the compounds of this invention, the radical $R_2$ is alkyl or perfluoroalkyl each of 1-12 carbon atoms. Among such compounds, preferred compounds are those in which $R_2$ is alkyl of 1-8 carbon atoms and in particular of 1-4 carbon atoms. Among the analogous perfluoroalkyl derivatives, those in which $R_2$ is of not more than 6 and preferably of 1-4 carbon atoms, and in particular is trifluoromethyl, are preferred.

The compounds of this invention are prepared in the manner customary for such substances. Preferably, an acetophenone of Formula II

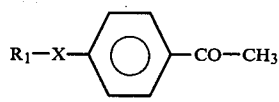 (II)

in which $R_1$ is as defined in Formula I, is reacted in the presence of a basic condensing agent with a carboxylic acid ester of Formula III

 (III)

in which Z is a lower alkyl group and $R_2$ is as defined in Formula I, and the initially resulting salt of the enol form of the diketone (I) is hydrolyzed to the ketone.

The acetophenones of Formula II are known from the literature in some cases, or they can be prepared analogously to the compounds of this type which are known from the literature, in particular by acetylation of a compound of Formula IV

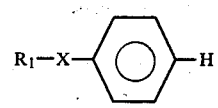 (IV)

under the conventional conditions of a Friedel-Crafts reaction. In the carboxylic acid esters of Formula III, Z is usually an alkyl group of not more than 4 carbon atoms, preferably methyl or ethyl. These esters are known from the literature.

The reaction of the acetophenones of Formula II with the esters of Formula III is carried out under the conditions generally customary for Claisen condensations of this type, the basic condensing agents used being, in particular, sodium, potassium, sodium amide, potassium amide, sodium hydride or sodium alcoholates or potassium alcoholates. Preferably, the reactions are carried out in an anhydrous, inert organic solvent, for example, diethyl ether, tetrahydrofuran, benzene, toluene, xylene or petroleum ether. In most cases, the alkali metal salt of the enol form of the diketone of Formula I is formed, as a solid precipitate, in this reaction, which preferably is carried out at a temperature of $-20°$ C. to $+50°$ C. This precipitate is filtered off, washed with pure solvent and hydrolyzed with water, optionally in the presence of a small amount of a mineral acid. If the hydrolysis is carried out in the presence of an organic solvent which is immiscible with water, the organic phase containing the diketone (I) is subsequently separated off and evaporated. The residual diketone is then purified by recrystallization from a suitable solvent, for example, methanol, ethanol or ethyl acetate.

Furthermore, the diketones of this invention of Formula I can be prepared by reacting a benzoic acid ester of Formula V

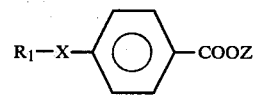 (V)

in which $R_1$ and Z are as defined above, with a ketone of the Formula VI

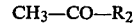 (VI)

under conditions which are substantially analogous to those for the reaction of the acetophenones II with the carboxylic acid esters III. In these preparative reactions, for those products requiring a trans-cyclohexyl group as defined above, the corresponding cyclohexyl-containing starting material will contain its cyclohexyl ring also in the trans-position. That is, configuration of the cyclohexyl ring is retained in these preparative reactions. The cyclohexyl configurations of the starting materials in each case are commercially available or are readily preparable using fully conventional methods, such as those disclosed in German Offenlegungsschriften Nos. 26 36 684 and 27 01 591.

The compounds of Formula I are valuable components of liquid crystal dielectrics, which are used to produce electro-optical display elements. The fact that the compounds can be used for this purpose is probably due to the existence of the tautomeric enol structures VIIa and VIIb

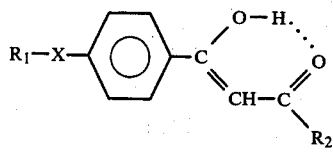 (VIIa)

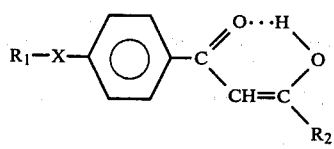 (VIIb)

This assumption is also supported by the ability of the diketones of this invention to form complex salts.

The liquid crystal dielectrics of this invention consist of two or more components, including at least one of Formula I. The other components are preferably nematic or nematogenic substances from the categories of the azobenzenes, azoxybenzenes, biphenyls, Schiff's bases, in particular benzylidene derivatives, phenyl benzoates, phenylcyclohexanes, optionally halogenated stilbenes, diphenylacetylene derivatives, diphenylnitrones and substituted cinnamic acids. The most important compounds which can be used as other components of this type can be characterized by Formula VIII:

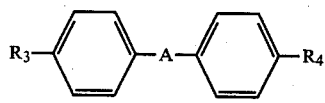 (VIII)

in which A is

—CH=CH—

—CX'=CH—

—CH=CX'—

—C≡C—

—N=N—

—N(O)=N—

—N=N(O)—
—O—CO—
—CO—O—
—S—CO—

—CH=N—
—N=CH—
—CH=N(O)—
—N(O)=CH—

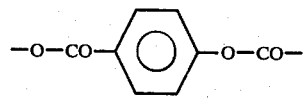

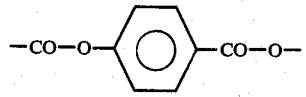

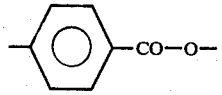

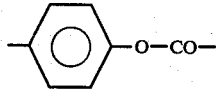

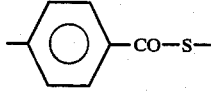

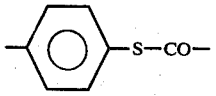

| -continued | |
|---|---|
| —CO—S— | or a C—C single bond. |

Other possible components of the dielectrics of this invention are those compounds of Formula VIII in which one or more phenyl rings have been replaced by a corresponding number of trans-cyclohexyl rings. X' is halogen, preferably Cl. $R_3$ and $R_4$ are identical or different and can be alkyl, alkoxy, alkanoyl, alkanoyloxy or alkoxycarbonyloxy each of not more than 18 and preferably not more than 8 carbon atoms; furthermore, one of these radicals can also be a cyano, nitro or isonitrile group. In most of these compounds, $R_3$ and $R_4$ are preferably different and one of the radicals is usually an alkyl or alkoxy group. However, a large number of other variants of the envisaged substituents are also customary. Many such substances are available commercially.

The dielectrics of this invention contain as a rule at least 30, preferably 50–99 and in particular 60–98 parts by weight of the compounds of the Formulae I and, optionally, VIII, per 100 total weight parts of dielectric. Of this amount preferably at least 15 parts by weight and usually even 20 or more parts by weight are made up by one or more compounds of Formula I. However, it is also possible to prepare dielectrics of this invention which consist exclusively of two or more compounds of Formula I. On the other hand, the invention also comprises those liquid crystal dielectrics to which, for example, for doping purposes, only less than 15 parts by weight, for example, 0.1 to 3 parts by weight, of one or more compounds of Formula I have been added.

The dielectrics of this invention are prepared in a manner which is in itself customary. As a rule, the desired amount of one or more compounds of Formula I is dissolved in any additional components which may be present, preferably at elevated temperature. If the temperature chosen is above the clear point of the base material, it is particularly easy to observe when the dissolving process has gone to completion.

It is, however, also possible to mix solutions of the components of the Formulae I and, optionally, VIII, in a suitable organic solvent, for example, acetone, chloroform or methanol, and, after thorough mixing, to remove the solvent again, for example, by distillation under reduced pressure. Of course, with this procedure care must be taken that no impurities or undesired doping agents are carried in by the solvent.

By means of suitable additives, the liquid crystal dielectrics of this invention can be so modified that they can be used in all types of liquid crystal display elements disclosed hitherto. Such additives are known to those skilled in the art and are described in detail in the relevant literature. For example, substances for changing the dielectric anisotropy, the viscosity, the conductivity and/or the orientation of the nematic phases can be added. Such substances are described, for example, in German Offenlegungsschriften Nos. 2,209,127, 2,240,864, 2,321,632, 2,338,281 and 2,450,088. Doping agents and dichroitic dyes include, e.g., substituted hydroquinone dibenzoate derivatives, azobenzene derivatives, 4-alkylcyclohexane carboxylic esters, methine 4-nitroarylidene dyes, stilbene derivative dichroic dyes or tris-azo dichroic dyes, respectively disclosed in, e.g., U.S. Pat. Nos. 4,099,856, 4,105,654, 4,113,647, 4,105,299, 4,116,861, or 4,128,497.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point and Cl. the clear point of a liquid crystal substance in degrees centigrade; boiling points are designated b.p.

EXAMPLE 1

A solution of 265 g of 4-(4-n-pentylphenyl)-acetophenone in 300 ml of ethyl acetate is added to 1 liter of anhydrous diethyl ether which contains 23 g of sodium in the form of a wire. The reaction mixture is stirred for 24 hours at room temperature. The sodium salt which has precipitated is then filtered off and washed with diethyl ether and introduced into a shaking vessel, with 500 ml of diethyl ether and 500 ml of water. After shaking for 1 hour, the organic phase is separated off, dried over sodium sulphate and evaporated. The residual 1-[4-n-pentylbiphenyl-(4')-yl]-butane-1,3-dione is recrystallized from ethanol; m.p. 110°, Cl. 135°.

The following compounds are prepared analogously:
1-[4-(4-methylcyclohexyl)-phenyl]-butane-1,3-dione
1-[4-(4-ethylcyclohexyl)-phenyl]-butane-1,3-dione
1-[4-(4-n-propylcyclohexyl)-phenyl]-butane-1,3-dione, m.p. 99.5°, Cl. 30°
1-[4-(4-n-butylcyclohexyl)-phenyl]-butane-1,3-dione, m.p. 94°, Cl. 87°
1-[4-(4-n-pentylcyclohexyl)-phenyl]-butane-1,3-dione, m.p. 81°, Cl. 97°
1-[4-(4-n-hexylcyclohexyl)-phenyl]-butane-1,3-dione
1-[4-(4-n-heptylcyclohexyl)-phenyl]-butane-1,3-dione, m.p. 74°. Cl. 98°
1-[4-(4-n-octylcyclohexyl)-phenyl]-butane-1,3-dione
1-[4-(4-n-nonylcyclohexyl)-phenyl]-butane-1,3-dione
1-[4-(4-n-decylcyclohexyl)-phenyl]-butane-1,3-dione
1-[4-(4-n-undecylcyclohexyl)-phenyl]-butane-1,3-dione
1-[4-(4-n-dodecylcyclohexyl)-phenyl]-butane-1,3-dione
1-[4-(4-methylcyclohexyl)-biphenyl-(4')-yl]-butane-1,3-dione
1-[4-(4-ethylcyclohexyl)-biphenyl-(4')-yl]-butane-1,3-dione
1-[4-(4-n-propylcyclohexyl)-biphenyl-(4')-yl]-butane-1,3-dione
1-[4-(4-n-butylcyclohexyl)-biphenyl-(4')-yl]-butane-1,3-dione
1-]4-(4-n-pentylcyclohexyl)-biphenyl-(4')-yl]-butane-1,3-dione
1-[4-(4-n-hexylcyclohexyl)-biphenyl-(4')-yl]-butane-1,3-dione
1-[4-(4-n-heptylcyclohexyl)-biphenyl-(4')-yl]-butane-1,3-dione
1-[4-(4-n-octylcyclohexyl)-biphenyl-(4')-yl]-butane-1,3-dione
1-[4-(4-n-nonylcyclohexyl)-biphenyl-(4')-yl]-butane-1,3-dione
1-[4-(4-n-decylcyclohexyl)-biphenyl-(4')-yl]-butane-1,3-dione
1-[4-(4-n-undecylcyclohexyl)-biphenyl-(4'-)yl]-butane-1,3-dione
1-[4-(4-n-dodecylcyclohexyl)-biphenyl-(4')-yl]-butane-1,3-dione
4-[4-(4-methylcyclohexyl)-phenyl]-pentane-1,3-dione
1-[4-(4-ethylcyclohexyl)-phenyl]-pentane-1,3-dione
1-[4-(4-n-propylcyclohexyl)-phenyl]-pentane-1,3-dione, m.p. 78°, Cl. 84°
1-[4-(4-n-butylcyclohexyl)-phenyl]-pentane-1,3-dione
1-[4-(4-n-pentylcyclohexyl)-phenyl]-pentane-1,3-dione m.p. 59°, Cl. 91°
1-[4-(4-n-hexylcyclohexyl)-phenyl]-pentane-1,3-dione
1-[4-(4-n-heptylcyclohexyl)-phenyl]-pentane-1,3-dione
1-[4-(4-n-octylcyclohexyl)-phenyl]-pentane-1,3-dione
1[4-(4-n-nonylcyclohexyl)-phenyl]-pentane-1,3-dione
1-[4-(4-n-decylcyclohexyl)-phenyl]-pentane-1,3-dione
1-[4-(4-n-undecylcyclohexyl)-phenyl]-pentane-1,3-dione
1-[4-(4-n-dodecylcyclohexyl)-phenyl]-pentane-1,3-dione
1-[4-(4-methylcyclohexyl)-biphenyl-(4')-yl]-pentane-1,3-dione
1-[4-(4-ethylcyclohexyl)-biphenyl-(4')-yl]-pentane-1,3-dione
1-[4-(4-n-propylcyclohexyl)-biphenyl-(4')-yl]-pentane-1,3-dione
1-[4-(4-n-butylcyclohexyl)-biphenyl-(4')-yl]-pentane-1,3-dione
1-[4-(4-n-pentylcyclohexyl)-biphenyl-(4')-yl]-pentane-1,3-dione
1-[4-(4-n-hexylcyclohexyl)-biphenyl-(4')-yl]-pentane-1,3-dione
1-[4-(4-n-heptylcyclohexyl)-biphenyl-(4')-yl]-pentane-1,3-dione
1-[4-(4-n-octylcyclohexyl)-biphenyl-(4')-yl]-pentane-1,3-dione
1-[4-(4-n-nonylcyclohexyl)-biphenyl-(4')-yl]-pentane-1,3-dione
1-[4-(4-n-decylcyclohexyl)-biphenyl-(4')-yl]-pentane-1,3-dione
1-[4-(4-n-undecylcyclohexyl)-biphenyl-(4')-yl]-pentane-1,3-dione
1-[4-(4-n-dodecylcyclohexyl)-biphenyl-(4')-yl]-pentane-1,3-dione
1-[4-(4-methylcyclohexyl)-phenyl]-hexane-1,3-dione
1-[4-(4-ethylcyclohexyl)-phenyl]-hexane-1,3-dione
1-[4-(4-n-propylcyclohexyl)-phenyl]-hexane-1,3-dione, m.p. 99°, Cl. 100°
1-[4-(4-n-butylcyclohexyl)-phenyl]-hexane-1,3-dione
1-[4-(4-n-pentylcyclohexyl)-phenyl]-hexane-1,3-dione
1-[4-(4-n-hexylcyclohexyl)-phenyl]-hexane-1,3-dione
1-[4-(4-n-heptylcyclohexyl)-phenyl]-hexane-1,3-dione
1-[4-(4-n-octylcyclohexyl)-phenyl]-hexane-1,3-dione
1-[4-(4-n-nonylcyclohexyl)-phenyl]-hexane-1,3-dione
1-[4-(4-n-decylcyclohexyl)-phenyl]-hexane-1,3-dione
1-[4-(4-n-undecylcyclohexyl)-phenyl]-hexane-1,3-dione
1-[4-(4-n-dodecylcyclohexyl)-phenyl]-hexane-1,3-dione
1-[4-(4-methylcyclohexyl)-biphenyl-(4')-yl]-hexane-1,3-dione
1-[4-(4-ethylcyclohexyl)-biphenyl-(4')-yl]-hexane-1,3-dione
1-[4-(4-n-propylcyclohexyl)-biphenyl-(4')-yl]-hexane-1,3-dione
1-[4-(4-n-butylcyclohexyl)-biphenyl-(4')-yl]-hexane-1,3-dione
1-[4-(4-n-pentylcyclohexyl)-biphenyl-(4')-yl]-hexane-1,3-dione
1-[4-(4-n-hexylcyclohexyl)-biphenyl-(4')-yl]-hexane-1,3-dione
1-[4-(4-n-heptylcyclohexyl)-biphenyl-(4')-yl]-hexane-1,3-dione 1-[4-(4-n-octylcyclohexyl)-biphenyl-(4')-yl]-hexane-1,3-dione
1-[4-(4-n-nonylcyclohexyl)-biphenyl-(4')-yl]-hexane-1,3-dione
1-[4-(4-n-decylcyclohexyl)-biphenyl-(4')-yl]-hexane-1,3-dione
1-[4-(4-n-undecylcyclohexyl)-biphenyl-(4')-yl]-hexane-1,3-dione
1-[4-(4-n-dodecylcyclohexyl)-biphenyl-(4')-yl]-hexane-1,3-dione
1-[4-(4-methylcyclohexyl)-phenyl]-heptane-1,3-dione
1-[4-(4-ethylcyclohexyl)-phenyl]-heptane-1,3-dione
1-[4-(4-n-propylcyclohexyl)-phenyl]-heptane-1,3-dione, m.p. 90°, Cl. 75°
1-[4-(4-n-butylcyclohexyl)-phenyl]-heptane-1,3-dione
1-[4-(4-n-pentylcyclohexyl)-phenyl]-heptane-1,3-dione
1-[4-(4-n-hexylcyclohexyl)-phenyl]-heptane-1,3-dione
1-[4-(4-n-heptylcyclohexyl)-phenyl]-heptane-1,3-dione
1-[4-(4-n-octylcyclohexyl)-phenyl]-heptane-1,3-dione
1-[4-(4-n-nonylcyclohexyl)-phenyl]-heptane-1,3-dione
1-[4-(4-n-decylcyclohexyl)-phenyl]-heptane-1,3-dione
1-[4-(4-n-undecylcyclohexyl)-phenyl]-heptane-1,3-dione
1-[4-(4-n-dodecylcyclohexyl)-phenyl]-heptane-1,3-dione
1-[4-(4-methylcyclohexyl)-biphenyl-(4')-yl]-heptane-1,3-dione
1-[4-(4-ethylcyclohexyl)-biphenyl-(4')-yl]-heptane-1,3-dione
1-[4-(4-n-propylcyclohexyl)-biphenyl-(4')-yl]-heptane-1,3-dione
1-[4-(4-n-butylcyclohexyl)-biphenyl-(4')-yl]-heptane-1,3-dione
1-[4-(4-n-pentylcyclohexyl)-biphenyl-(4')-yl]-heptane-1,3-dione
1-[4-(4-n-hexylcyclohexyl)-biphenyl-(4')-yl]-heptane-1,3-dione
1-[4-(4-n-heptylcyclohexyl)-biphenyl-(4')-yl]-heptane-1,3-dione
1-[4-(4-n-octylcyclohexyl)-biphenyl-(4')-yl]-heptane-1,3-dione
1-[4-(4-n-nonylcyclohexyl)-biphenyl-(4')-yl]-heptane-1,3-dione
1-[4-(4-n-decylcyclohexyl)-biphenyl-(4')-yl]-heptane-1,3-dione
1-[4-(4-n-undecylcyclohexyl)-biphenyl-(4')-yl]-heptane-1,3-dione
1-[4-(4-n-dodecylcyclohexyl)-biphenyl-(4')-yl]-heptane-1,3-dione
1-[4-(4-methylcyclohexyl)-phenyl]-4,4,4-trifluorobutane-1,3-dione
1-[4-(4-ethylcyclohexyl)-phenyl]-4,4,4-trifluorobutane-1,3-dione
1-[4-(4-n-propylcyclohexyl)-phenyl]-4,4,4-trifluorobutane-1,3-dione
1-[4-(4-n-butylcyclohexyl)-phenyl]-4,4,4-trifluorobutane-1,3-dione
1-[4-(4-n-pentylcyclohexyl)-phenyl]-4,4,4-trifluorobutane-1,3-dione, m.p. 65°, Cl. 40°
1-[4-(4-n-hexylcyclohexyl)-phenyl]-4,4,4-trifluorobutane-1,3-dione
1-[4-(4-n-heptylcyclohexyl)-phenyl]-4,4,4-trifluorobutane-1,3-dione
1-[4-(4-n-octylcyclohexyl)-phenyl]-4,4,4-trifluorobutane-1,3-dione
1-[4-(4-n-nonylcyclohexyl)-phenyl]-4,4,4-trifluorobutane-1,3-dione
1-[4-(4-n-decylcyclohexyl)-phenyl]-4,4,4-trifluorobutane-1,3-dione
1-[4-(4-n-undecylcyclohexyl)-phenyl]-4,4,4-trifluorobutane-1,3-dione
1-[4-(4-n-dodecylcyclohexyl)-phenyl]-4,4,4-trifluorobutane-1,3-dione
1-[4-(4-methylcyclohexyl)-biphenyl-(4')-yl]-4,4,4-trifluorobutane-1,3-dione
1-[4-(4-ethylcyclohexyl)-biphenyl-(4')-yl]-4,4,4-trifluorobutane-1,3-dione
1-[4-(4-n-propylcyclohexyl)-biphenyl-(4')-yl]-4,4,4-trifluorobutane-1,3-dione
1-[4-(4-n-butylcyclohexyl)-biphenyl-(4')-yl]-4,4,4-trifluorobutane-1,3-dione
1-[4-(4-n-pentylcyclohexyl)-biphenyl-(4')-yl]-4,4,4-trifluorobutane-1,3-dione
1-[4-(4-n-hexylcyclohexyl)-biphenyl-(4')-yl]-4,4,4-trifluorobutane-1,3-dione
1-[4-(4-n-heptylcyclohexyl)-biphenyl-(4')-yl]-4,4,4-trifluorobutane-1,3-dione
1-[4-(4-n-octylcyclohexyl)-biphenyl-(4')-yl]-4,4,4-trifluorobutane-1,3-dione
1-[4-(4-n-nonylcyclohexyl)-biphenyl-(4')-yl]-4,4,4-trifluorobutane-1,3-dione
1-[4-(4-n-decylcyclohexyl)-biphenyl-(4')-yl]-4,4,4-trifluorobutane-1,3-dione
1-[4-(4-n-undecylcyclohexyl)-biphenyl-(4')-yl]-4,4,4-trifluorobutane-1,3-dione
1-[4-(4-n-dodecylcyclohexyl)-biphenyl-(4')-yl]-4,4,4-trifluorobutane-1,3-dione
1-[4-methylbiphenyl-(4')-yl]-butane-1,3-dione
1-[4-ethylbiphenyl-(4')-yl]-butane-1,3-dione
1-[4-n-propylbiphenyl-(4')-yl]-butane-1,3-dione
1-[4-n-butylbiphenyl-(4')-yl]-butane-1,3-dione
1-[4-n-hexylbiphenyl-(4')-yl]-butane-1,3-dione
1-[4-n-heptylbiphenyl-(4')-yl]-butane-1,3-dione
1-[4-n-octylbiphenyl-(4')-yl]-butane-1,3-dione
1-[4-n-nonylbiphenyl-(4')-yl]-butane-1,3-dione
1-[4-n-decylbiphenyl-(4')-yl]-butane-1,3-dione
1-[4-n-undecylbiphenyl-(4')-yl]-butane-1,3-dione
1-[4-n-dodecylbiphenyl-(4')-yl]-butane-1,3-dione
1-[4-trifluoromethylbiphenyl-(4')-yl]-butane-1,3-dione
1-[4-methoxybiphenyl-(4')-yl]-butane-1,3-dione
1-[4-ethoxybiphenyl-(4')-yl]-butane-1,3-dione
1-[4-n-propyloxybiphenyl-(4')-yl]-butane-1,3-dione
1-[4-n-butyloxybiphenyl-(4')-yl]-butane-1,3-dione
1-[4-n-pentyloxybiphenyl-(4')-yl]-butane-1,3-dione
1-[4-n-hexyloxybiphenyl-(4')-yl]-butane-1,3-dione
1-[4-n-heptyloxybiphenyl-(4')-yl]-butane-1,3-dione
1-[4-n-octyloxybiphenyl-(4')-yl]-butane-1,3-dione
1-[4-n-nonyloxybiphenyl-(4')-yl]-butane-1,3-dione
1-[4-n-decyloxybiphenyl-(4')-yl]-butane-1,3-dione
1-[4-n-undecyloxybiphenyl-(4')-yl]-butane-1,3-dione
1-[4-n-dodecyloxybiphenyl-(4')-yl]-butane-1,3-dione
1-[4-methylbiphenyl-(4')-yl]-pentane-1,3-dione
1-[4-ethylbiphenyl-(4')-yl]-pentane-1,3-dione
1-[4-n-propylbiphenyl-(4')-yl]-pentane-1,3-dione
1-[4-n-butylbiphenyl-(4')-yl]-pentane-1,3-dione
1-[4-n-pentylbiphenyl-(4')-yl]-pentane-1,3-dione
1-[4-n-hexylbiphenyl-(4')-yl]-pentane-1,3-dione
1-[4-n-heptylbiphenyl-(4')-yl]-pentane-1,3-dione
1-[4-n-octylbiphenyl-(4')-yl]-pentane-1,3-dione
1-[4-n-nonylbiphenyl-(4')-yl]-pentane-1,3-dione
1-[4-n-decylbiphenyl-(4')-yl]-pentane-1,3-dione
1-[4-n-undecylbiphenyl-(4')-yl]-pentane-1,3-dione
1-[4-n-dodecylbiphenyl-(4')-yl]-pentane-1,3-dione
1-[4-trifluoromethylbiphenyl-(4')-yl]-pentane-1,3-dione
1-[4-methoxybiphenyl-(4')-yl]-pentane-1,3-dione 1-[4-ethoxybiphenyl-(4')-yl]-pentane-1,3-dione
1-[4-n-propyloxybiphenyl-(4')-yl]-pentane-1,3-dione
1-[4-n-butyloxybiphenyl-(4')-yl]-pentane-1,3-dione
1-[4-n-pentyloxybiphenyl-(4')-yl]-pentane-1,3-dione
1-[4-n-hexyloxybiphenyl-(4')-yl]-pentane-1,3-dione
1-[4-n-heptyloxybiphenyl-(4')-yl]-pentane-1,3-dione
1-[4-n-octyloxybiphenyl-(4')-yl]-pentane-1,3-dione
1-[4-n-nonyloxybiphenyl-(4')-yl]-pentane-1,3-dione
1-[4-n-decyloxybiphenyl-(4')-yl]-pentane-1,3-dione
1-[4-n-undecyloxybiphenyl-(4')-yl]-pentane-1,3-dione
1-[4-n-dodecyloxybiphenyl-(4')-yl]-pentane-1,3-dione
1-[4-methylbiphenyl-(4')-yl]-hexane-1,3-dione
1-[4-ethylbiphenyl-(4')-yl]-hexane-1,3-dione
1-[4-n-propylbiphenyl-(4')-yl]-hexane-1,3-dione
1-[4-n-butylbiphenyl-(4')-yl]-hexane-1,3-dione
1-[4-n-pentylbiphenyl-(4')-yl]-hexane-1,3-dione
1-[4-n-hexylbiphenyl-(4')-yl]-hexane-1,3-dione
1-[4-n-heptylbiphenyl-(4')-yl]-hexane-1,3-dione
1-[4-n-octylbiphenyl-(4')-yl]-hexane-1,3-dione
1-[4-n-nonylbiphenyl-(4')-yl]-hexane-1,3-dione
1-[4-n-decylbiphenyl-(4')-yl]-hexane-1,3-dione
1-[4-n-undecylbiphenyl-(4')-yl]-hexane-1,3-dione
1-[4-n-dodecylbiphenyl-(4')-yl]-hexane-1,3-dione
1-[4-trifluoromethylbiphenyl-(4')-yl]-hexane-1,3-dione
1-[4-methylbiphenyl-(4')-yl]-hexane-1,3-dione
1-[4-ethoxybiphenyl-(4')-yl]-hexane-1,3-dione
1-[4-n-propyloxybiphenyl-(4')-yl]-hexane-1,3-dione
1-[4-n-butyloxybiphenyl-(4')-yl]-hexane-1,3-dione
1-[4-n-pentyloxybiphenyl-(4')-yl]-hexane-1,3-dione
1-[4-n-hexyloxybiphenyl-(4')-yl]-hexane-1,3-dione
1-[4-n-heptyloxybiphenyl-(4')-yl]-hexane-1,3-dione
1-[4-n-octyloxybiphenyl-(4')-yl]-hexane-1,3-dione
1-[4-n-nonyloxybiphenyl-(4')-yl]-hexane-1,3-dione
1-[4-n-decyloxybiphenyl-(4')-yl]-hexane-1,3-dione
1-[4-n-undecyloxybiphenyl-(4')-yl]-hexane-1,3-dione
1-[4-n-dodecyloxybiphenyl-(4')-yl]-hexane-1,3-dione
1-[4-methylbiphenyl-(4')-yl]-heptane-1,3-dione
1-[4-ethylbiphenyl-(4')-yl]-heptane-1,3-dione
1-[4-n-propylbiphenyl-(4')-yl]-heptane-1,3-dione
1-[4-n-butylbiphenyl-(4')-yl]-heptane-1,3-dione
1-[4-n-pentylbiphenyl-(4')-yl]-heptane-1,3-dione
1-[4-n-hexylbiphenyl-(4')-yl]-heptane-1,3-dione
1-[4-n-heptylbiphenyl-(4')-yl]-heptane-1,3-dione
1-[4-n-octylbiphenyl-(4')-yl]-heptane-1,3-dione
1-[4-n-nonylbiphenyl-(4')-yl]-heptane-1,3-dione
1-[4-n-decylbiphenyl-(4')-yl]-heptane-1,3-dione
1-[4-n-undecylbiphenyl-(4')-yl]-heptane-1,3-dione
1-[4-n-dodecylbiphenyl-(4')-yl]-heptane-1,3-dione
1-[4-trifluoromethylbiphenyl-(4')-yl]-heptane-1,3-dione
1-[4-methoxybiphenyl-(4')-yl]-heptane-1,3-dione
1-[4-ethoxybiphenyl-(4')-yl]-heptane-1,3-dione
1-[4-n-propyloxybiphenyl-(4')-yl]-heptane-1,3-dione
1-[4-n-butyloxybiphenyl-(4')-yl]-heptane-1,3-dione
1-[4-n-pentyloxybiphenyl-(4')-yl]-heptane-1,3-dione
1-[4-n-hexyloxybiphenyl-(4')-yl]-heptane-1,3-dione
1-[4-n-heptyloxybiphenyl-(4')-yl]-heptane-1,3-dione
1-[4-n-octyloxybiphenyl-(4')-yl]-heptane-1,3-dione
1-[4-n-nonyloxybiphenyl-(4')-yl]-heptane-1,3-dione
1-[4-n-decyloxybiphenyl-(4')-yl]-heptane-1,3-dione
1-[4-n-undecyloxybiphenyl-(4')-yl]-heptane-1,3-dione
1-[4-n-dodecyloxybiphenyl-(4')-yl]-yl]-heptane-1,3-dione
1-[4-methylbiphenyl-(4')-yl]-4,4,4-trifluorobutane-1,3-dione
1-[4-ethylbiphenyl-(4')-yl]-4,4,4-trifluorobutane-1,3-dione
1-[4-n-propylbiphenyl-(4')-yl]-4,4,4-trifluorobutane-1,3-dione
1-[4-n-butylbiphenyl-(4')-yl]-4,4,4-trifluorobutane-1,3-dione
1-[4-n-pentylbiphenyl-(4')-yl]-4,4,4-trifluorobutane-1,3-dione
1-[4-n-hexylbiphenyl-(4')-yl]-4,4,4-trifluorobutane-1,3-dione
1-[4-n-heptylbiphenyl-(4')-yl]-4,4,4-trifluorobutane-1,3-dione
1-[4-n-octylbiphenyl-(4')-yl]-4,4,4-trifluorobutane-1,3-dione
1-[4-n-nonylbiphenyl-(4')-yl]-4,4,4-trifluorobutane-1,3-dione
1-[4-n-decylbiphenyl-(4')-yl]-4,4,4-trifluorobutane-1,3-dione
1-[4-n-undecylbiphenyl-(4')-yl]-4,4,4-trifluorobutane-1,3-dione
1-[4-n-dodecylbiphenyl-(4')-yl]-4,4,4-trifluorobutane-1,3-dione
1-[4-trifluoromethylbiphenyl-(4')-yl]-4,4,4-trifluorobutane-1,3-dione
1-[4-methoxybiphenyl-(4')-yl]-4,4,4-trifluorobutane-1,3-dione
1-[4-ethoxybiphenyl-(4')-yl]-4,4,4-trifluorobutane-1,3-dione
1-[4-n-propyloxybiphenyl-(4')-yl]-4,4,4-trifluorobutane-1,3-dione
1-[4-n-butyloxybiphenyl-(4')-yl]-4,4,4-trifluorobutane-1,3-dione
1-[4-n-pentyloxybiphenyl-(4')-yl]-4,4,4-trifluorobutane-1,3-dione
1-[4-n-hexyloxybiphenyl-(4')-yl]-4,4,4-trifluorobutane-1,3-dione
1-[4-n-heptyloxybiphenyl-(4')-yl]-4,4,4-trifluorobutane-1,3-dione
1-[4-n-octyloxybiphenyl-(4')-yl]-4,4,4-trifluorobutane-1,3-dione
1-[4-n-nonyloxybiphenyl-(4')-yl]-4,4,4-trifluorobutane-1,3-dione
1-[4-n-decyloxybiphenyl-(4')-yl]-4,4,4-trifluorobutane-1,3-dione
1-[4-n-undecyloxybiphenyl-(4')-yl]-4,4,4-trifluorobutane-1,3-dione and
1-[4-n-dodecyloxybiphenyl-(4')-yl]-4,4,4-trifluorobutane-1,3-dione.

The examples which follow relate to the use, according to this invention, of the diketones (I) as components of liquid crystal dielectrics:

EXAMPLE 2

A mixture of 46.7 parts by weight of 4-n-pentylphenyl anisate, 23.3 parts by weight of 4'-n-pentylphenyl-4-n-hexyloxybenzoate, 15.0 parts by weight of 1-[4-(4-n-pentylcyclohexyl)-phenyl]-pentane-1,3-dione, 7.5 parts by weight of 1-[4-(4-n-pentylcyclohexyl)-phenyl]-butane-1,3-dione and 7.5 parts by weight of 1-[4-(4-n-butylcyclohexyl)-phenyl]-butane-1,3-dione has a melting point of 5° and a clear point of 64°. 5 parts by weight of the dichroitic dye 1-hydroxy-4-N-(p-n-nonyloxyphenyl)-amino-anthraquinone can be dissolved in this mixture at 25° without difficulty.

EXAMPLE 3

A mixture of 58.0 parts by weight of 4-n-butyl-4'-methoxyazoxybenzene, 29.0 parts by weight of 4-ethyl-4'-methoxyazoxybenzene, 8.0 parts by weight of 2'-cyano-4'-n-heptylphenyl 4-n-heptylbiphenyl-(1)-carboxylate and 5.0 parts by weight of 1-[4-(4-n-pentylcyclohexyl)-phenyl]-butane-1,3-dione has a melting point of −4° and a clear point of 78°. Ethyl-dodecyl-dimethyl-ammonium 4-(4-n-hexyloxybenzene)-benzoate is readily soluble in the mixture; the dielectric thus obtained is outstandingly suitable for liquid crystal display elements based on the dynamic scattering effect. The dichroitic dye 1-hydroxy-4-N-(p-n-nonyloxphenyl)-amino-anthraquinone is also readily soluble in this mixture in amounts of up to 5%; these dye-containing dielectrics are particularly well suited for the preparation of colored display elements which operate on the basis of the deformation of aligned phases (DAP effect).

EXAMPLE 4

A mixture of 26.1 parts by weight of 4-(4-n-propylcyclohexyl)-benzonitrile, 36.9 parts by weight of 4-(4-n-pentylcyclohexyl)-benzonitrile, 27.0 parts by weight of 4-(4-n-heptylcyclohexyl)-benzonitrile, 5.0 parts by weight of 1-[4-(4-n-propylcyclohexyl)-phenyl]-4,4,4-trifluorobutane-1,3-dione and 5.0 parts by weight of 1-[4-(4-n-pentylcyclohexyl)-phenyl]-4,4,4-trifluorobutane-1,3-dione has a melting point of 0° and a clear point of 50°. Dichroitic dyes such as, for example, 1-hydroxy-4-N-(p-n-nonyloxyphenyl)-amino-anthraquinone, are readily soluble in this mixture; after customary doping with a chiral substance, the dielectrics obtained in this way make it possible to prepare a liquid crystal color switch with good contrast.

EXAMPLE 5

A mixture of 14 parts by weight of 1-[4-(4-n-butylcyclohexyl)-phenyl]-butane-1,3-dione, 14 parts by weight of 1-[4-(4-n-pentylcyclohexyl)-phenyl]-butane-1,3-dione, 14 parts by weight of 1-[4-(4-n-heptylcyclohexyl)-phenyl]-butane-1,3-dione, 29 parts by weight of 1-[4-(4-n-pentylcyclohexyl)-phenyl]-pentane-1,3-dione and 29 parts by weight of 1-(4-heptylphenyl)-butane-1,3-dione has a melting point of 20° and a clear point of 49°. The mixture possesses a negative dielectric anisotropy and a good dissolving power for dichroitic dyes or acetylacetonate complexes of polyvalent metal ions; such solutions possess an electrical conductivity which is carried, on the one hand, by the metal cations and, on the other hand, by the keto-enolate anions contained in the liquid crystal matrix.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystal dielectric, comprising at least two liquid crystal components, at least one being a diketone of the formula

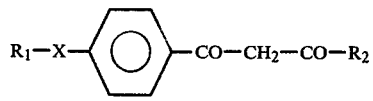

wherein $R_1$ is alkyl, perfluoroalkyl or alkoxy, each of 1–18 carbon atoms; $R_2$ is alkyl or perfluoroalkyl, each of 1–12 carbon atoms; and X is 1,4-trans-cyclohexylene, 1,4-phenylene or 4,4'-cyclohexylphenyl.

2. A composition comprising a diketone of the formula

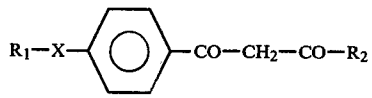

wherein $R_1$ is alkyl, perfluoroalkyl or alkoxy, each of 1–18 carbon atoms; $R_2$ is alkyl or perfluoroalkyl, each of 1–12 carbon atoms; and X is 1,4-trans-cyclohexylene, 1,4-phenylene or 4,4'-cyclohexylphenyl and a liquid crystal dielectric doping agent or dichroitic dye.

3. A liquid crystal dielectric of claim 1 wherein the diketone is of the formula

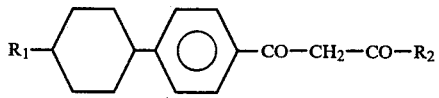

wherein $R_1$ is alkyl of 1–18 carbon atoms and $R_2$ is alkyl or perfluoroalkyl, each of 1–12 carbon atoms.

4. A liquid crystalline dielectric of claim 1 wherein the diketone is of the formula

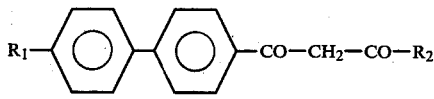

5. A liquid crystalline dielectric of claim 1 wherein the diketone is of the formula

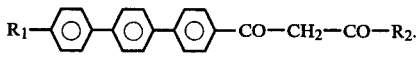

6. A liquid crystalline dielectric of claim 1 wherein in the diketone $R_2$ is $C_{1-8}$ alkyl.

7. In an electro-optical display element having a liquid crystal cell comprising a liquid crystal dielectric, the improvement wherein the dielectric is that of claim 1, 3, 4 or 5.

* * * * *